(12) United States Patent
Kuo et al.

(10) Patent No.: US 7,446,209 B2
(45) Date of Patent: Nov. 4, 2008

(54) SYNTHESIS OF TEMOZOLOMIDE AND ANALOGS

(75) Inventors: Shen-Chun Kuo, Union, NJ (US); Janet L. Mas, Green Brook, NJ (US); Donald Hou, Newtown, PA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/453,125

(22) Filed: Jun. 14, 2006

(65) Prior Publication Data

US 2006/0229456 A1    Oct. 12, 2006

Related U.S. Application Data

(62) Division of application No. 11/040,784, filed on Jan. 21, 2005, now abandoned, which is a division of application No. 10/050,488, filed on Jan. 16, 2002, now Pat. No. 7,087,751.

(60) Provisional application No. 60/262,465, filed on Jan. 18, 2001.

(51) Int. Cl.
C07D 233/66    (2006.01)
C07D 487/04    (2006.01)

(52) U.S. Cl. .................................. 548/326.5; 544/179

(58) Field of Classification Search ............. 548/326.5; 544/182; 514/241
See application file for complete search history.

(56) References Cited

U.S. PATENT DOCUMENTS

| 3,941,768 | A | 3/1976 | Stocker |
| 5,003,099 | A | 3/1991 | Mettler |
| 5,260,291 | A | 11/1993 | Lunt |
| 5,824,346 | A | 10/1998 | Dugan |
| 5,939,098 | A | 8/1999 | Reidenberg |
| 5,942,247 | A | 8/1999 | Dugan |
| 6,096,757 | A | 8/2000 | Bishop |
| 6,251,886 | B1 | 6/2001 | Friedman |
| 6,316,462 | B1 | 11/2001 | Bishop |
| 6,333,333 | B1 | 12/2001 | Bishop |
| 6,346,524 | B1 | 2/2002 | Ragab |

FOREIGN PATENT DOCUMENTS

| EP | 0113570 | 7/1984 |
| EP | 02252682 | 7/1987 |
| GB | 2125402 | 8/1983 |
| JP | 53-18521 | 2/1978 |
| JP | 53-34745 | 3/1978 |
| JP | 53-127413 | 11/1978 |
| JP | 54-14932 | 2/1979 |
| JP | 54-41830 | 4/1979 |
| JP | 54-59283 | 5/1979 |
| JP | 54-70232 | 6/1979 |
| JP | 54-70233 | 6/1979 |
| JP | 54-73737 | 6/1979 |
| JP | 54-102127 | 8/1979 |
| JP | 54-130598 | 10/1979 |
| JP | 55-9654 | 1/1980 |
| JP | 55-17349 | 2/1980 |
| JP | 2000-327648 | 11/2000 |

OTHER PUBLICATIONS

Whitehead, "The reactions of orthoesters with ureas. A new synthesis of pyrimidines" Journal Am. Chem. Society 75:671-675(1953).

O'Donnell, et al. "The synthesis of amino acid derivatives by catalytic phase-transfer alkylations" Tetrahedron Letters 47:4625-4628(1978).

O'Donnell, et al. "A mild and efficient route to Schiff Base derivatives of amino acids" J. Org. Chem. 47:2663-2666(1982).

Stevens, et al., "Antitumor Imidazotetrazines . . . Agent" Journal of Medicinal Chemistry 27(2):196-201 (1984).

Bhawal, et al, "Rapid, low-temperature amidation of ethyl cyanoacetate with lithium amides derived from primary and secondary amines" Synthetic Communications 20(20):3235-3243(1990).

Tsang, et al., "Comparison of the cytotoxicity in vitro of temozolomide and dacarbazine, prodrugs of 3-methyl-(triazen-1-yl)imidazole-4-carboxamide" Cancer Chemother Pharmacol 27:342-346 (1991).

Newlands, et al., "Phase I trial of temozolomide (CCRG 81045: M&B 39831: NSC 362856)" Br. J. Cancer 65:287-291 (1992).

Stevens, et al., "From Triazines and Triazenes to Temozolomide" Eur. J. Cancer 29A(7):1045-1047 (1993).

Wang, et al., "Alternative Syntheses of the antitumor drug temozolomide avoiding the use of methyl isocyanates", Journal of Chemical Society, Chemical Communication, Chemical Society, Letchworth, GB, p. 1687-1688 (1994).

Wang, et al., "Antitumor imidazotetrazines. Part 33. new syntheses of the antitumor drug temozolomide using 'masked' methyl isocyanates", J. Chem. Soc., Perkin Trans. 1(21):2783-2787 (1995).

Wang, et al., "Synthetic studies of 8-carbamoylimidzo-'5, 1-DI-1, 2, 3, 5-tetrazi n-4(3H)- one: a key derivative of antitumor drug temozolomide", Bioorg. Med. Chem. Lett., 6(2):185-188 (1996).

Yongfeng Wang, "A new route to the antitumor drug temozolomide, but not thiotemozolomide", Chem. Commun., 4:363-364 (1997).

Wang, et al., "Antitumor Imidazotetrazines. 35. New Synthetic Routes to the Antitumor Drug Temozolomide", J. org. Chem. 62(21):7228-7294 (1997).

Wang, et al., Antitumor Imidazotetrazines. Part 36. Conversion of 5-Amino-Imidazole-4-Carboxamide to . . . Journal of the Chemical Society, Perkin Transactions 1, Chemical Society, Letchworth, GB, 10:1669-1675 (1998).

Primary Examiner—Venkataraman Balasubram
(74) Attorney, Agent, or Firm—Patent Practitioners of Schering Corporation

(57)    ABSTRACT

This invention relates to a novel process for the synthesis of Temozolomide, an antitumor compound, and analogs, and to intermediates useful in this novel process.

4 Claims, No Drawings

SYNTHESIS OF TEMOZOLOMIDE AND ANALOGS

REFERENCE TO RELATED APPLICATIONS

This application is a divisional application of, and claims the priority of U.S. patent application Ser. No. 11/040,784 filed Jan. 21, 2005, which application is a divisional application of U.S. patent application Ser. No. 10/050,488, filed Jan. 16, 2002, which application in turn is based on and claims the priority of U.S. Provisional Application No. 60/262,465, filed Jan. 18, 2001, each of which earlier applications is incorporated herein by reference in their entirety.

FIELD OF THE INVENTION

This invention relates to a novel process for the synthesis of Temozolomide, an antitumor compound, and analogs, and to intermediates useful in this novel process.

BACKGROUND OF THE INVENTION

Temozolomide, 3-methyl-8-aminocarbonyl-imidazo[5,1-d]-1,2,3,5-tetrazin-4(3H)-one, is a known antitumor drug; see for example Stevens et al., *J. Med. Chem.* 1984, 27, 196-201, and Wang et al., *J. Chem. Soc., Chem. Commun.*, 1994, 1687-1688. It has the formula:

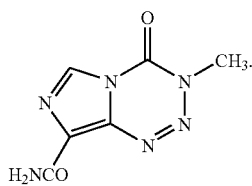

It is described in U.S. Pat. No. 5,260,291 (Lunt et al.) together with compounds of broadly similar activity such as higher alkyl analogs at the 3-position.

The synthesis of I by the process described in *J. Med. Chem.* 1984, 27, 196-201 can be simply depicted as follows, even though the authors mention that the cycloaddition of the methylisocyanate to the compound of the formula (B) can proceed through two different intermediates:

Scheme I:

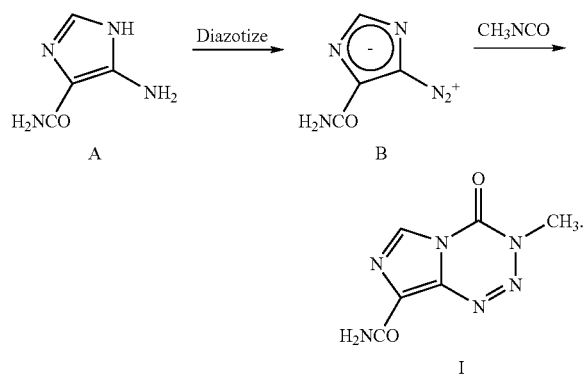

In this process, 5-amino-1H-imidazole-4-carboxamide (A) is converted into 5-diazo-1H-imidazole-4-carboxamide (B), which is then cyclized with methylisocyanate in dichloromethane to provide a high yield of clinical-grade Temozolomide. However, this process requires isolation of the unstable and potentially dangerous 5-diazo-1H-imidazole-4-carboxamide (B). Moreover, methylisocyanate is a difficult reagent to handle and ship, especially on the industrial scale, and indeed is better avoided in industrial manufacture. Furthermore, the cycloaddition of methylisocyanate requires a very long reaction time: Table I in *J. Med. Chem.* 1984, 27, 196-201, suggests 20 days.

The production of I by the two processes described in *J. Chem. Soc., Chem. Commun.*, 1994, 1687-1688 provides a low overall yield from 5-amino-1H-imidazole-4-carboxamide (A): less than 20% (unoptimized—about 17% through 5-diazo-1H-imidazole-4-carboxamide (B) and about 15% through 5-amino-$N^1$-(ethoxycarbonylmethyl)-1H-imidazole-1,4-dicarboxamide (C)):

Scheme II:

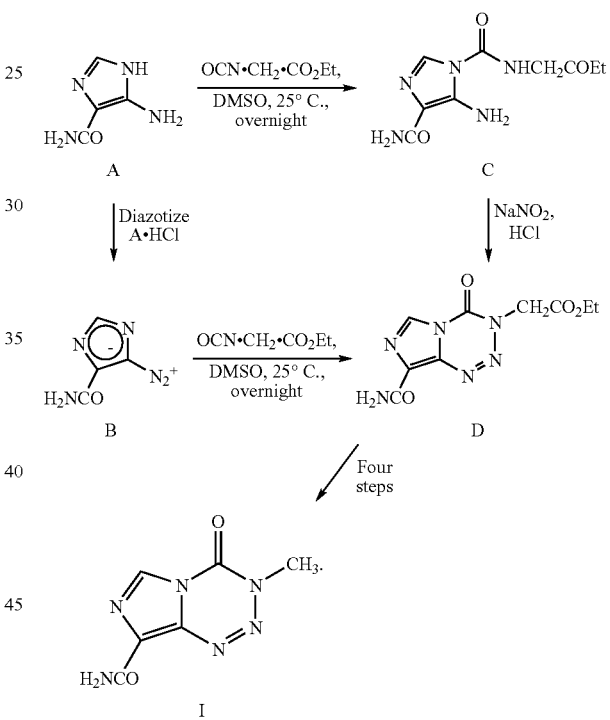

Moreover, the unstable 5-diazo-1H-imidazole-4-carboxamide (B) still has to be isolated in the branch of this process that uses it as an intermediate.

Clearly, therefore, there is a need for synthetic methods that are more convenient, especially on an industrial scale, and provide good yields of clinical-grade Temozolomide, or improve the preparation or use of intermediates for the aforementioned processes.

SUMMARY OF THE INVENTION

The present invention provides, as one embodiment, a process for the preparation of Temozolomide and lower alkyl analogs thereof having the formula:

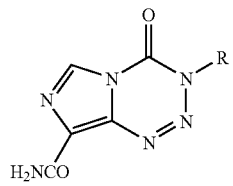

wherein R is an alkyl group having from 1 to 6 carbon atoms, which comprises:

(a) diazotizing a compound of the formula:

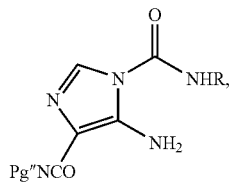

wherein R is as defined above;

and Pg" is a divalent protecting group that is readily removable by hydrolysis or hydrogenolysis; or two monovalent protecting groups Pg that are readily removable by hydrolysis or hydrogenolysis; or a bulky monovalent protecting group Pg that is readily removable by hydrolysis or hydrogenolysis, together with a hydrogen atom;

and thereafter (b) subjecting the resulting compound of the formula:

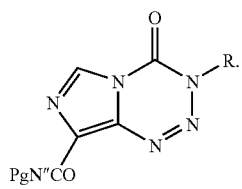

wherein Pg" is as defined above, to hydrolysis or hydrogenolysis.

Step (a) is preferably carried out in an aqueous-organic solution with a source of nitrous acid, in particular in solution in an aqueous organic acid such as a lower alkanoic acid, especially acetic acid. Water-miscible solvents such as lower alkanols, THF and DMF can be present. The source of nitrous acid is preferably inorganic, e.g., an alkali metal salt of nitrous acid, most preferably sodium nitrite. The reaction is preferably carried out in the presence of a reagent that promotes the correct direction of cyclization, e.g., LiCl.

Step (b) is preferably carried out by hydrolysis with a strong mineral acid such as concentrated HCl or HBr, or $HClO_4$, $CF_3SO_3H$, or $MeSO_3H$, or especially concentrated sulfuric acid, at a moderate temperature such as −20 to 50° C. In a particularly preferred embodiment, the readily-removable protecting group is a 1,1-dimethylethyl group (a t-butyl group), together with a hydrogen atom. Its bulk also helps to promote the correct direction of cyclization.

The invention also provides novel intermediates useful in the preparation of Temozolomide, in particular the compounds of the formulae II, III, IV, V, and VI, and the salts thereof:

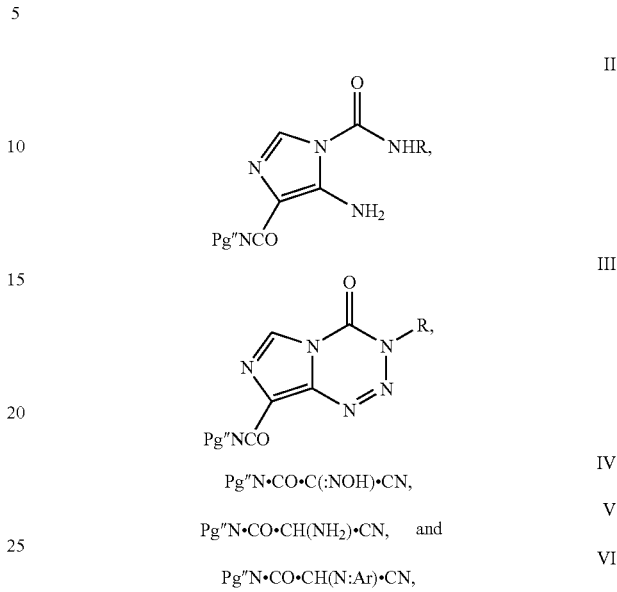

wherein Pg" is a protecting group as defined above, especially such compounds wherein Pg" is a 1,1-dimethylethyl group together with a hydrogen atom, Ar is an arylmethylene group, and R is a lower alkyl group as hereinbefore defined, especially a methyl group. An especially preferred arylmethylene group is the diphenylmethylene group; preferred compounds of the formulae II and III include the compounds of the formulae:

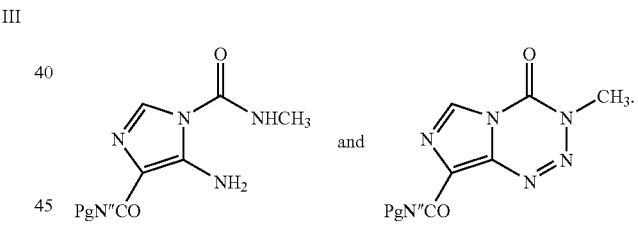

DETAILED DESCRIPTION OF THE PREFERRED EMBODIMENTS

It should be noted that the cyclization of the compound of the formula II above, wherein Pg" is a monovalent protecting group Pg together with a hydrogen atom, could in theory also proceed to the nitrogen atom of the carbamoyl group, and yield an undesired aza-hypoxanthine derivative. The presence of a bulky protecting group Pg promotes the desired cyclization to the imidazo[5,1-d]-1,2,3,5-tetrazine nucleus of Temozolomide. The presence of LiCl in the reaction medium also has a beneficial effect in promoting the desired cyclization. The complete blocking of the nitrogen atom by the use of a divalent protecting group or two monovalent protecting groups also ensures that the cyclization proceeds in the desired direction.

The 1,1-dimethylethyl group was formerly known as t-butyl, sometimes abbreviated to t-Bu, and this old form of the name is still used herein (for convenience and especially brevity) in some of the formulae herein and in the semi-trivial names in the reaction schemes and in the Examples.

The alkyl group R is preferably an unbranched alkyl group, in particular one with 1 to 4 carbon atoms, preferably 1-butyl, 1-propyl, ethyl or especially methyl. When R is methyl, the product of the formula I is Temozolomide itself.

A particularly preferred embodiment of the process according to the invention is shown in the following scheme, and a more general version of this scheme is described thereafter:

Scheme III:

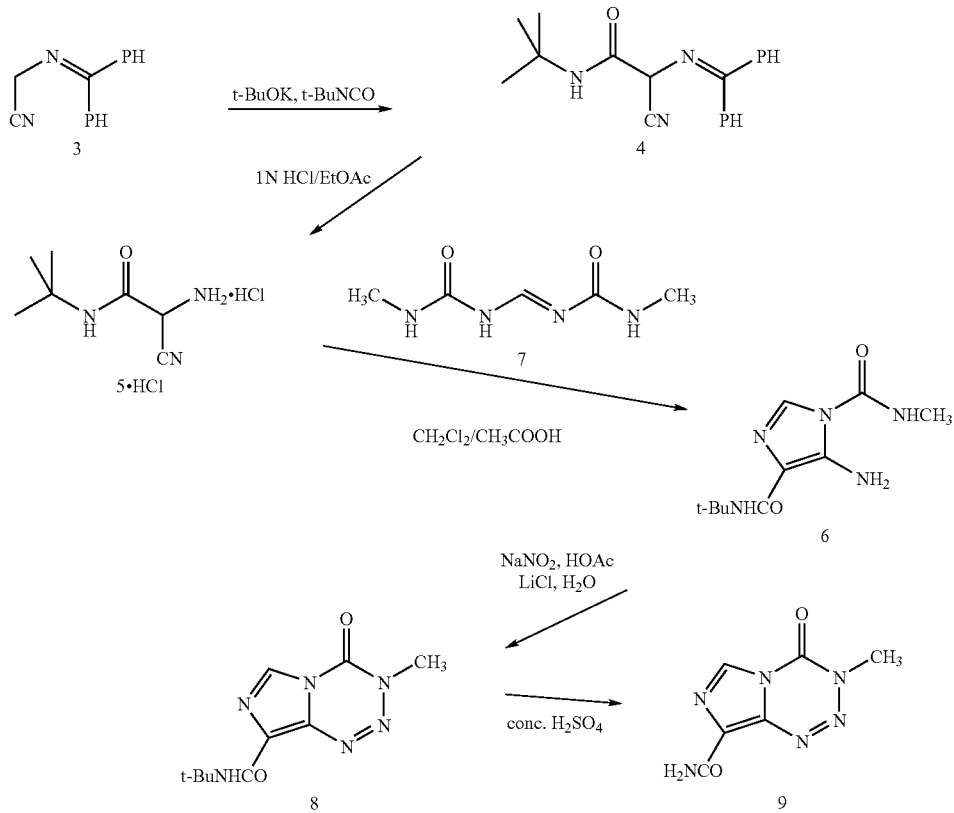

In the first step of this process, [(diphenylmethylene)amino]acetonitrile 3 is allowed to react with an isocyanate PgNCO where Pg is a monovalent protecting group as defined above, to yield an acetamide 4. This reaction is conveniently effected in the presence of a base and of an inert organic solvent, under an inert atmosphere, e.g., nitrogen, and at a ambient temperature or reduced temperature, e.g., ambient temperature to −100° C., preferably ambient temperature to −10° C. The base is preferably one having the formula PgOM, where M is an alkali metal; other bases that can be used include tertiary amines such as triethylamine and ethyldiisopropylamine, alkali metal hydrides such as sodium and potassium hydride, and alkali metal carbonates such as sodium and potassium carbonate. The organic solvent is preferably methylene chloride; however, other solvents that can be used include ethers such as methyl-t-butylether, diethylether, THF and dioxane, methylcyanide, ethylacetate, and hydrocarbons such as toluene, hexane and heptane.

The protecting group Pg is preferably a bulky alkyl group, e.g., one that is strongly branched at the carbon atom having the free valency, especially a 1,1-dimethylethyl group. Other possible monovalent protecting groups, some of which can be removed by hydrolysis, whereas others can be removed by hydrogenation, include benzyl (or phenylmethyl), especially two benzyl groups, trityl (or triphenylmethyl), benzyloxycarbonyl, and 9-fluorenyl. Divalent protecting groups that may be used include benzylidene (or phenylmethylene) and 9-fluorenylidene. Further examples of suitable amino-protecting groups, and their use and removal, are given in "Protective Groups in Organic Synthesis", Theodora Greene and Peter Wuts, John Wiley & Sons, New York, N.Y., second edition (1991).

A divalent protecting group Pg" or two monovalent protecting groups $Pg_2$ can be introduced by an analogous reaction in which the t-BuNCO is replaced by a compound of the formula Pg":N.CO.Cl, wherein Pg" is a divalent protecting group or two monovalent protecting groups Pg; this reaction is also effected in the presence of a base and an inert organic solvent substantially as described above. The compound of the formula Pg":N.CO.Cl can be prepared by reaction of an imine or amine of the formula Pg":NH with phosgene.

In the second step of this process, the acetamide 4 is subjected to hydrolysis to remove the diphenylmethylene group (an example of the group Ar) on the imino nitrogen, preferably with mild acid in an aqueous or aqueous-organic system, especially a mild inorganic acid (such as dilute mineral acid, e.g. 1N hydrochloric acid, hydrobromic acid or sulfuric acid) in an inert organic solvent such as ethyl acetate; the product is the acetamide 5, as an acid addition salt such as the hydrochloride, hydrobromide or sulfate. The hydrolysis is conveniently effected at 0° C. to moderately elevated temperature, e.g., 100° C., especially ambient temperature up to 70° C.

In the third step of this process, a salt, e.g., the hydrochloride, of the acetamide 5 is condensed with a urea derivative 7 or with analogs thereof on which each methyl group has been replaced with a group R, wherein the two groups R are identical and each group R is as defined above. The urea derivative can be replaced with precursors thereof, e.g., the N—R-urea wherein R is as defined above (especially N-methylurea), together with an orthoformate, e.g. ethyl orthoformate, to provide the imidazole 6. This reaction can be carried out at about ambient temperature in the presence of an inert organic solvent and a mild acidic catalyst. The catalyst can be an organic acid, preferably a weak acid such as a carboxylic acid, especially a lower alkanoic acid such as acetic acid; the solvent is for example t-BuOMe or preferably methylene chloride. The organic solvent is preferably methylene chloride; however, other solvents that can be used include ethers such as methyl-t-butylether, diethylether, THF and dioxane, methylcyanide, ethylacetate, DMF, DMSO, and hydrocarbons such as toluene, hexane and heptane. The reaction is preferably carried out at about ambient temperature or somewhat lower or higher, e.g., −25 to 50° C., preferably 0 to 35° C.

Urea derivatives necessary for the fourth step can be prepared by condensation of the N—R-urea wherein R is as defined above, especially N-methylurea with an orthoester, especially an orthoformate; thus methyl[[[(methylamino)carbonyl]amino]methylene]urea 7 can be prepared by condensation of N-methylurea with ethyl orthoformate at elevated temperature and under an inert atmosphere; see Whitehead, C. W.; J. Am. Chem. Soc., 1953, 75, 671.

In the fourth step of this process, the imidazo[5,1-d]-1,2,3,5-tetrazine nucleus of Temozolomide is assembled by diazotization of the imidazole 6 or N—R analog thereof, wherein R is as defined above; preferred conditions have been described above.

The reaction can also be effected in an organic solvent with an organic source of nitrous acid, e.g., t-butyl or isopentyl nitrite with a carboxylic acid such as a lower alkanoic acid, e.g., acetic acid, and in an organic solvent such as a lower alkanol, DMF, THF, ethyl acetate, or a hydrocarbon such as toluene, hexane or heptane.

The reaction presumably proceeds through a diazonium salt, which spontaneously cyclizes to the compound of the formula III.

In the fifth step of this process, Temozolomide or N-alkyl analog thereof (wherein the alkyl group has 1 to 6 carbon atoms) is produced by hydrolysis of the protected-Temozolomide 8 or protected-N-alkyl analog thereof; again, the conditions have been described above.

The protected-Temozolomide 8 or protected-N-alkyl analog thereof (wherein the alkyl group has 1 to 6 carbon atoms) is an example of a compound of the formula III. In general, hydrolysis to remove a protecting group is preferably carried out under an inert atmosphere and at a moderate temperature, e.g., at about 0° C. to 50° C., preferably about ambient temperature, in an aqueous acid. Alternatively, the hydrolysis can be carried out in an inert organic solvent in which the reagents (the acid and the compound 8) are at least partly soluble, for example, methylene chloride. Hydrogenolysis to remove a protecting group is preferably carried out under an inert atmosphere and at a moderate temperature, e.g., at about ambient temperature to about 60° C., in an inert organic solvent with hydrogen and a hydrogenation catalyst such as Pd/C or Raney Ni.

The compound of the formula 3 is known and can be prepared by the following known process:

Scheme IV:

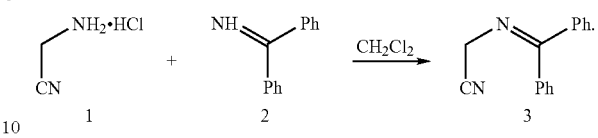

(See, for example, O'Donnell, M. J.; Polt, R. L; J. Org. Chem., 1982, 47, 2663; and O'Donnell, M. J.; Eckrich, T. M.; Tetrahedron Lett. 1978, 47, 4625.) Aminoacetonitrile 1 (preferably as an acid addition salt, e.g., the hydrochloride) is condensed with imine 2 in the presence of an anhydrous, inert organic solvent and under an inert atmosphere. The imine provides a protecting group for the amino group of the aminoacetonitrile, a group that is stable to alkali but can be readily removed with mild acid when no longer needed. An aralkylidene-imine, especially a diphenylmethylidene-imine, is convenient. The organic solvent is conveniently methylene chloride.

In the compounds of the formula 3 and 4, the amino-protecting group (Ph)$_2$C: can be replaced with another appropriate protecting group of the formula Ar, where Ar is as hereinbefore defined. In the compounds of the formulae 4, 5, 6, and 8, the 1,1-dimethylethylamino group can be replaced with another appropriate protected amino group Pg$_2$N— or Pg":N—, where Pg and Pg" are as hereinbefore defined.

The compound of the formula 5 can be prepared also by the following novel method:

Scheme V:

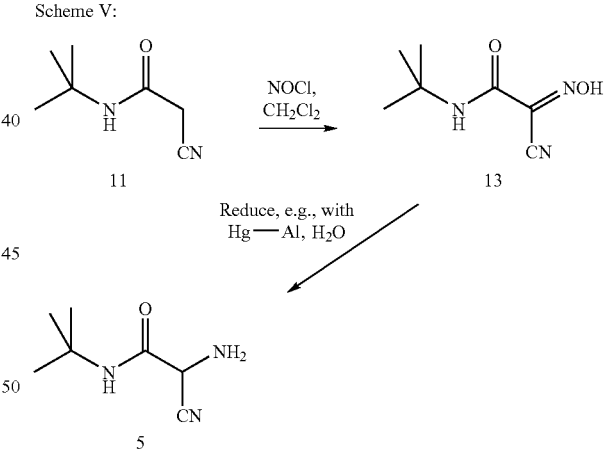

2-Cyano-N-(1,1-dimethylethyl)acetamide 11 (Bhawal, B. M.; Khanapure, S. P.; Biehl, E. R.; Syn. Commun., 1990, 20, 3235) is allowed to react with nitrosyl chloride in an inert organic solvent such as CH$_2$Cl$_2$ or CHCl$_3$ at moderate temperature (e.g., ambient temperature to −25° C., preferably about 0° C.). The resulting 2-cyano-N-(1,1-dimethylethyl)-2-(hydroxyimino)acetamide 13 is isolated and reduced, for example with sodium dithionite in an aqueous organic solvent, but preferably with aluminum amalgam in water at moderate temperature (e.g., ambient temperature to about 0° C., preferably about 0° C.).

The compound of the formula 13 is a novel intermediate and is a feature of the invention. The compound of the formula 13 forms salts with strong bases, e.g., with alkali metals such as sodium, and these salts are also a feature of the invention. Further features of the invention include compounds analogous to 13 wherein the 1,1-dimethylethylamino group is replaced by a protected amino group Pg"N, where Pg" is as hereinbefore defined. Such compounds can be prepared analogously from the compound of the formula 10 and a compound of the formula HN:Pg", wherein Pg" is as defined above, especially a divalent group such as benzylidene or 9-fluorenylidene, or two monovalent groups Pg such as two benzyl groups, or a monovalent group such as benzyl, trityl, benzyloxycarbonyl, or 9-fluorenyl, together with a hydrogen atom.

5-Amino-1H-imidazole-4-carboxamide, the intermediate of the formula (A) described in the 'Background of the Invention', can be advantageously prepared (e.g., as its hydrochloride 16.HCl) by the two routes shown in Scheme VI, wherein 17 is a novel intermediate, 14 is commercially available and a method for its preparation is given in U.S. Pat. No. 5,003,099, and the preparation of 6 has been described above. These present an improvement also in the preparation of Temozolomide, since the starting material of the formula (A) (for the diazotization in both Schemes I and II above) is made more readily and/or more cheaply available. Again, if desired, the N-methyl groups in the compounds of the formulae 6, 7 and 15 can be replaced with larger groups R, wherein R is as defined above.

Scheme VI:

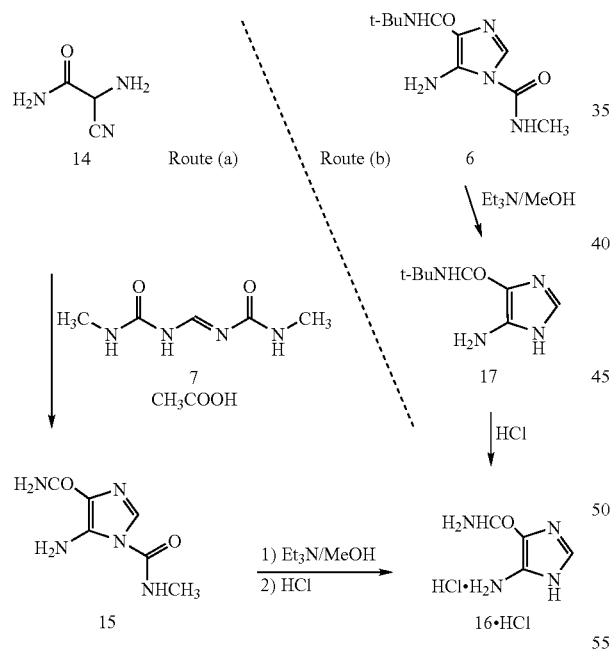

In route (a), purified aminocyanoacetamide 14 (obtained for example by recrystallization, e.g., from acetone) is condensed with a urea derivative 7 or with analogs thereof in which each methyl group has been replaced with a group R, wherein the two groups R are identical and each group R is as defined above. The urea derivative can be replaced with precursors thereof, e.g., the N—R-urea wherein R is as defined above (especially N-methylurea), together with an orthoformate, e.g. ethyl orthoformate, to provide the imidazole 15. This reaction can be carried out as described above for the reaction of 5 with 7 or with precursors of 7. Imidazole 15 (or an analog thereof in which the methyl group has been replaced with a group R, wherein R is as defined above), can then be hydrolyzed with mild base, e.g., a tertiary organic base such as triethylamine or ethyldiisopropylamine in an inert organic solvent such as a lower alkanol, e.g., methanol, and the product 16 can then be converted into its acid addition salt by reaction with the appropriate acid, e.g., the hydrochloride of 16 (or other salt as described in the next paragraph) by reaction with hydrochloric acid, preferably in an inert organic solvent such as a lower alkanol, e.g., methanol or ethanol, an ether such as methyl-t-butylether, diethylether, THF or dioxane, methylcyanide, ethylacetate, or a hydrocarbon such as toluene, hexane or heptane.

In route (b), imidazole 6 (or an analog thereof in which the methyl group has been replaced with a group R, wherein R is as defined above) can be converted into another imidazole derivative 17 by hydrolysis with a mild base as described above for the first step of the conversion of imidazole 15 into 16.HCl; and the free base can then be subjected to removal of the protecting 1,1-dimethylethylamino group, and converted in the same step into an acid addition salt, e.g., 16.HCl, preferably under conditions as described above for the second step of the conversion of imidazole 15 into 16.HCl. The acid used in this step is preferably a strong acid, e.g., a mineral acid such as HCl (to provide 16.HCl), or HBr, $H_2SO_4$, $HClO_4$ or $HNO_3$, or a strong organic acid such as $CF_3SO_3H$ or $CH_3SO_3H$. The solvent may be aqueous or, especially when the acid is $CF_3SO_3H$ or $CH_3SO_3H$, organic.

The compound of the formula 6 is named as a starting material in the novel process according to the invention, but can also be used as a novel starting material for the intermediates in the known process for the preparation of Temozolomide. Further compounds that can be used in both these aspects include compounds analogous to the compound of the formula 6 and having the formula II, and higher alkyl analogs of the compound of the formula 6.

Preferred intermediates of the formulae VI and V include:

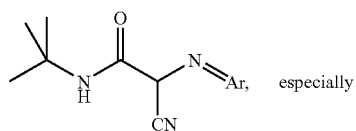 especially

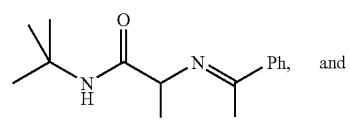 and

4

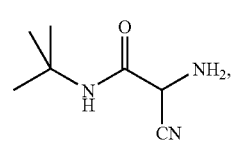

5 wherein Ar is as hereinbefore defined but is preferably a diphenylmethylene group.

In the compounds of the formulae 4, 5, 6, 8, 11, 13 and 17, and also the compound of the formula t-Bu.NH.CO.C(N:Ar).CN, the 1,1-dimethylethylamino group can be replaced with a protected amino group PgNH, Pg$_2$N, or Pg"N, where Pg and Pg" are as hereinbefore defined.

The invention also provides a process for the preparation of a compound of the formula IV, which comprises:

1. amidation of the ester group with a protecting amine, preferably 1,1-dimethylethylamine and especially in the presence of a basic catalyst and an inert organic solvent;

2. nitrosylation of the reactive methylene group, e.g., with an alkali metal nitrite, e.g., sodium nitrite, and a weak acid such as an organic acid, especially acetic acid, but preferably with nitrosyl chloride in an inert organic solvent such as methylene chloride.

The resulting compound has the formula Pg"N.CO.C(: NOH).CN wherein Pg" is a protecting group, especially a 1,1-dimethylethyl group together with a hydrogen atom. Compounds of this formula and the intermediates of the formulae Pg"N.CO.CH$_2$.CN and Pg"N.CO.CH(N:Ar).CN are also features of the invention, especially those wherein Pg" is a 1,1-dimethylethyl group, together with a hydrogen atom.

The invention also provides a process for the preparation of the above-mentioned compound of the formula 8, which comprises diazotizing a compound of the formula II wherein Pg"N is a 1,1-dimethylethylamino group together with a hydrogen atom. This reaction can be effected under the reaction conditions set out under paragraph (a) at the start of the section Summary of the Invention.

Compounds of the formulae II, III, V and VI can exist in the form of their salts, for example with mineral acids, especially with hydrochloric acid and sulfuric acid. A particularly preferred salt of this type is compound 5.HCl.

Compounds of the formulae IV can exist in the form of their salts with bases, for example with alkali metals such as sodium.

The invention is not restricted to the specific embodiments of the processes shown in the foregoing Schemes III to VI and the specific intermediates used therein, but further comprises analogous processes which are carried out under different but substantially equivalent conditions, and also analogous processes and intermediates wherein different but broadly equivalent protecting groups Pg" and Ar are used, and especially those wherein the methyl group (the precursor of the 3-methyl group in Temozolomide) is replaced with a larger alkyl group R, wherein R is as hereinabove defined. Furthermore, the intermediates 4, 5, 6, 8, 13, and 17, which are novel, can also be modified to include different but broadly equivalent protecting groups Pg or Pg" and Ar, and intermediates 6 and 8 can be modified to include a larger alkyl group R (wherein Pg, Pg", Ar and R are as hereinabove defined). All these embodiments are features of the present invention.

It should be noted that the unfused imidazole nucleus can generally exist in two tautomeric forms (whose interconversion is catalyzed by acids), as illustrated in the following scheme for the compound of formula (A) above:

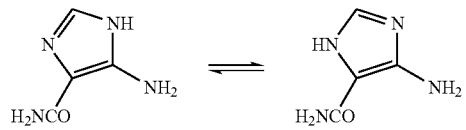

Although one such form may predominate, both formulae of such compounds are generally covered in the description and claims of this specification, even where the name or formula specifically identifies only one.

When used herein, the following terms have the indicated meanings:

alkyl—represents a saturated hydrocarbon group having 1 to 6 carbon atoms, preferably 1 to 4, which may be straight or branched but is preferably unbranched, e.g., 1-butyl, 1-propyl, ethyl, or especially methyl;

arylmethylene—represents a methylene group in which at least one aryl group as defined below is substituted for at least one of the methylene hydrogen atoms. In compounds such as that of formula V, the methylene carbon atom of the arylmethylene group is doubly bonded to the adjacent nitrogen atom. Representative arylmethylene groups include diphenylmethylene, phenylmethylene, and 9-fluorenylidene;

aryl (including the aryl portion of arylmethylene)—represents a carbocyclic group having from 6 to 14 carbon atoms and having at least one fused benzenoid ring, with all available substitutable carbon atoms of the carbocyclic group being intended as possible points of attachment, said carbocyclic group being optionally substituted with 1 to 3 Y groups, where each group Y is independently selected from halo, alkyl, nitro, alkoxy and dialkylamino groups. Preferred aryl groups are phenyl, substituted phenyl, 1-naphthyl, 2-naphthyl and indanyl.

EXAMPLES

The following Examples illustrate but do not in any way limit the present invention:

Example 1

3-Methyl-8-aminocarbonyl-imidazo[5,1-d]-1,2,3,5-tetrazin-4(3H)-one (Temozolomide)

Step A: Preparation of 2-cyano-N-(1,1-dimethylethyl)-2-[(diphenylmethylene)amino]-acetamide

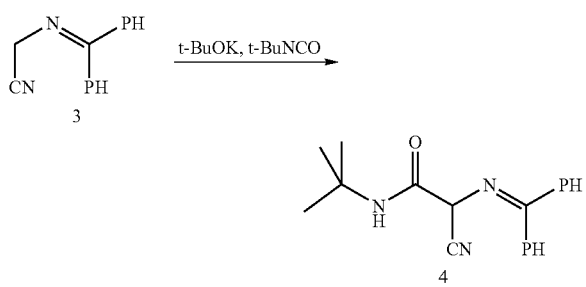

The imine 3 (700 g, 3.178 mol) and CH$_2$Cl$_2$ (7 L) were placed into a 22 L three-necked flask equipped with a nitrogen inlet, a gas outlet tube, reflux condenser, thermometer, mechanical stirrer, and maintained under a positive pressure of nitrogen. 1,1-Dimethylethyl-isocyanate (442 mL, 3.870 mol) was added to this stirred mixture at 0° C., and after stirring for 10 min a solution of potassium t-butoxide in THF (1.0 M in THF, 3.88 L, 3.88 mol) (as supplied by Aldrich) was added slowly (1 hour). The solution was stirred at 0° C. for 4 hours, when the reaction mixture had become a very thick paste with a deep brown color, and thin layer chromatography (EtOAc/hexanes=1/4) indicated that no more starting material was present. The resulting mixture was quenched with saturated NH$_4$Cl solution (5 L), and the organic layer was separated and washed sequentially with saturated NH$_4$Cl solution (5 L), and brine (5 L). The combined aqueous solution was extracted with CH$_2$Cl$_2$ (1 L). The combined CH$_2$Cl$_2$ solutions were dried over MgSO$_4$ and concentrated under reduced pressure to yield a brown solid. The resulting crude N-(1,1-dimethylethyl)-acetamide derivative was purified by slurrying in hexane (2.5 L) at a concentration of 1-5% at room temperature. The slurry was filtered and the filter cake dried in a vacuum oven (20 mm Hg, 20° C., 18 hours) to yield 0.914 kg (2.862 mol, 90%) N-(1,1-dimethylethyl)-acetamide derivative 4 as a brownish solid.

$^1$H NMR (400 MHz, CDCl$_3$, δ): 7.62 (d, 2H), 7.53 (m, 4H), 7.41 (m, 2H), 7.22 (m, 2H), 4.62 (s, 1H), 1.41 (s, 9H); mp: 107-108° C.

Step B: Preparation of 2-amino-2-cyano-N-(1,1-dimethylethyl)-acetamide hydrochloride, 5.HCl

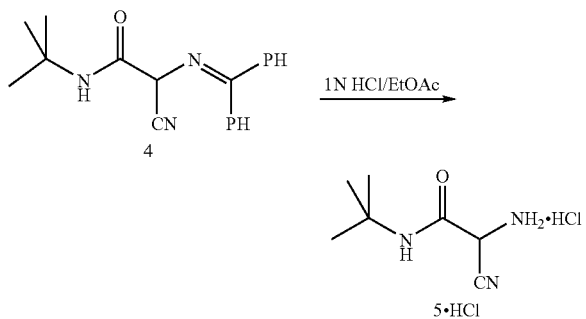

2-Cyano-N-(1,1-dimethylethyl)-2-[(diphenylmethylene)amino]acetamide 4 (900 g, 2.818 mol), ethyl acetate (4.5 L) and aqueous HCl (1 N, 4.5 L) were placed into a 12 L three-necked flask equipped with a nitrogen inlet, a gas outlet tube, reflux condenser, thermometer, mechanical stirrer, and maintained under a positive pressure of nitrogen. The mixture was heated on an oil bath at 60° C. for 4 hours with vigorous stirring, gradually cooled to room temperature, and then slowly diluted with CH$_2$Cl$_2$ (4 L). (Thin layer chromatography (EtOAc/hexanes=1/4) indicated no more starting material was present.) The resulting layers were separated and the aqueous phase was extracted with CH$_2$Cl$_2$ (4 L). The combined organic solutions were extracted with aqueous HCl (1N, 2×0.5 L). The aqueous extracts were combined and concentrated under reduced pressure to yield 490 g (2.557 mol) of 2-amino-2-cyano-N-(1,1-dimethylethyl)-acetamide hydrochloride 5.HCl.

$^1$H NMR (400 MHz, DMSO, δ): 9.38 (bs, 2H), 8.92 (s, 1H), 5.28 (s, 1H), 1.30 (s, 9H); mp: 211° C. (dec.)

Step G: Preparation of 5-Amino-N$^4$-(1,1-dimethylethyl)-N$^1$-methyl-1H-imidazole-1,4-dicarboxamide 6

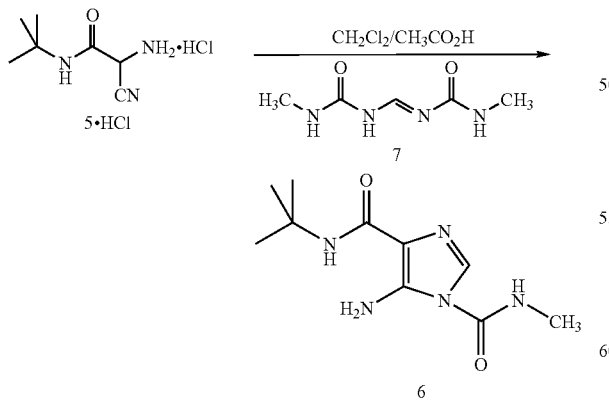

2-Amino-2-cyano-N-(1,1-dimethylethyl)-acetamide hydrochloride 5.HCl (414 g, 2.160 mol), urea 7 (414 g, 2.617 mol) (Whitehead, C. W.; J. Am. Chem. Soc., 1953, 75, 671), CH$_2$Cl$_2$ (4 L) and acetic acid (20 mL) were placed into a 10 L, three-necked flask equipped with a nitrogen inlet, a gas outlet tube, reflux condenser, thermometer, mechanical stirrer, and maintained under a positive pressure of nitrogen. The mixture was stirred vigorously at room temperature for 18 hours and then concentrated under reduced pressure. The residue was treated with H$_2$O (3 L) and stirred for 30 min, and the solids were collected by vacuum filtration. The solid was dried in an oven (20 mm Hg, 20° C., 18 hours) to yield 240 g of a grayish solid (0.943 mol, 94% pure, HPLC analysis). A standard sample of 5-amino-N$^4$-(1,1-dimethylethyl)-N$^1$-methyl-1H-imidazole-1,4-dicarboxamide 6 was prepared by recrystallization from EtOAc; mp: 145-147° C.

The aqueous solution was extracted with CH$_2$Cl$_2$ (2 L), the organic extract concentrated under reduced pressure, and the residue was washed sequentially with H$_2$O (200 mL) and EtOAc/hexanes (1/9, 500 mL) to yield 130 g of additional grayish product (0.505 mol, 93% pure, HPLC assay).

$^1$H NMR (400 MHz, CDCl$_3$, δ): 7.45 (s, 1H), 6.98 (bs, 1H), 6.50 (s, 1H), 5.92 (bs, 2H), 2.92 (d, 3H), 1.40 (s, 9H).

Although it was observed that smaller-scale reactions (using 1-15 g of 5) gave higher percentage yields of relatively purer product (e.g., 90-95% yield, 93-98% pure), such small-scale reactions are less practical for the preparation of a commercial product.

Purification of 5-Amino-N$^4$-(1,1-dimethylethyl)-N$^1$-methyl-1H-imidazole-1,4-dicarboxamide 6

5-Amino-N$^4$-(1,1-dimethylethyl)-N$^1$-methyl-1H-imidazole-1,4-dicarboxamide 6 (313 g, 93% pure by HPLC analysis) was suspended in EtOAc (4 L) and refluxed for 10 min. The solution was filtered while hot to remove solid residue, and was then cooled slowly to room temperature. The resulting solid product was collected by vacuum filtration. The filtrate was concentrated under reduced pressure to a thick paste and then filtered to afford an additional solid product. The combined solids were purified by slurrying in t-BuOMe/2-PrOH (1.5 L, 9/1) at room temperature for 1 hour. The solid product 6 was collected by filtration and was dried in a vacuum oven (20 mm Hg, room temperature, 48 hours) to yield 252 g of a tan-colored solid (98% pure against a standard sample by HPLC analysis). A satisfactory $^1$H NMR spectrum was obtained.

Step D: 3,4-Dihydro-N-(1,1-dimethylethyl)-3-methyl-imidazo[5,1-d]-1,2,3,5-tetrazine-8-carboxamide 8 (t-butyl-Temozolomide)

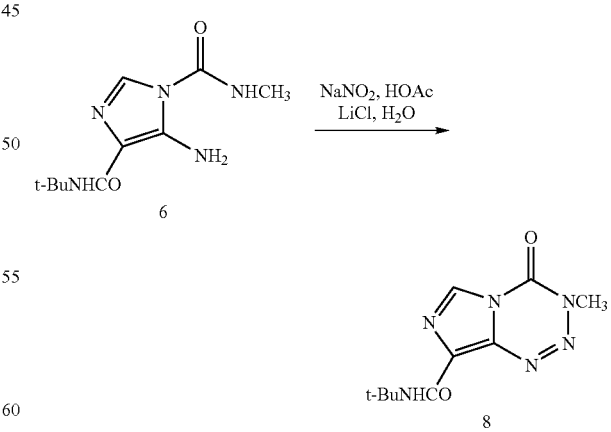

LiCl (45 g, 1.066 mol) (Aldrich), distilled H$_2$O (100 mL) and glacial acetic acid (2.5 mL, 43.9 mmol) were placed into a 500 ml three-necked flask equipped with an overhead mechanical stirrer and thermometer. The warm solution was stirred for 30 min in an ice bath until cooled to room temperature. 5-Amino-$N^4$-(1,1-dimethylethyl)-$N^1$-methyl-1H-imidazole-1,4-dicarboxamide 6 (5.0 g, 20.9 mmol, 98% pure) was then added, the mixture was stirred for 30 min, and then $NaNO_2$ (1.9 g, 23 mmol) (Fischer) was added. The reaction mixture was stirred at 0° C. for one hour and then at room temperature for 5 hours (when HPLC indicated that no more starting material was present), and then diluted with $CH_2Cl_2$ (100 mL). The resulting layers were separated and the aqueous phase was extracted with $CH_2Cl_2$ (100 mL). The combined organic solutions were washed with aqueous $Na_2S_2O_4$ (10 g/100 ml) and then with aqueous $NaHCO_3$ (saturated, 100 mL). The organic solution was concentrated under reduced pressure to afford 2 as a yellow-brown solid (4.56 g, 88% pure, HPLC assay). A standard sample was prepared by flash chromatography (6:4, EtOAc:hexane) twice. Satisfactory $^1$H and $^{13}$C NMR spectra and elemental analyses were obtained; mp: 135-136° C.

$^1$H NMR (400 MHz, $CDCl_3$, δ): 8.38 (s, 1H), 7.20 (bs, 1H), 4.04 (s, 3H), 1.52 (s, 9H).

Step E: 3-Methyl-8-aminocarbonyl-imidazo[5,1-d]-1,2,3,5-tetrazin-4(3H)-one 9 (Temozolomide)

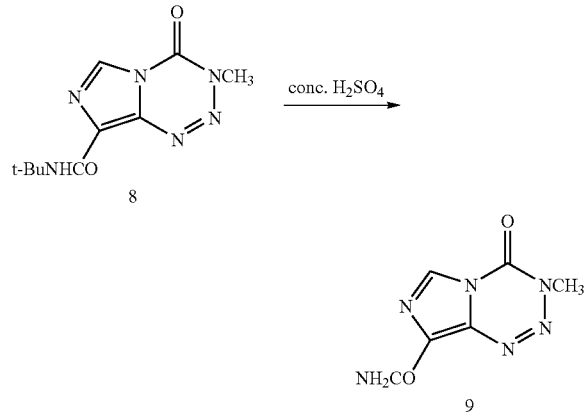

t-Butyl-Temozolomide 8 (4.01 g, 16.023 mmol) and conc. $H_2SO_4$ (8 mL) (Fisher Scientific) were placed into a 50 mL flask equipped with a stirrer bar. The mixture was stirred for 2 hours at room temperature and then slowly poured into ice-cold EtOH (160 mL). A white precipitate formed, which was collected by vacuum filtration and washed with ice-cold EtOH (10 mL). The solid was dried under vacuum (20 mm Hg, room temperature, 72 hours) to yield 2.63 g of 9 (13.546 mmol, 98.4% pure against a standard sample by HPLC analysis)

The mother liquors contained an additional 9.7% of 9 (HPLC assay).

Example 2

Preparation of Intermediates and Reagents

Part A: 2-Cyano-N-(1,1-dimethylethyl)-2-(hydroxyimino)acetamide 13

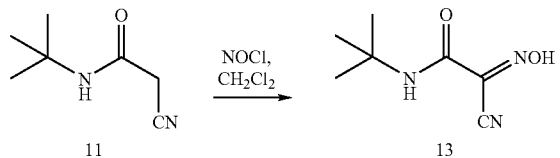

Amide 11 (3.11 g, 22.18 mmol) (Bhawal, B. M.; Khanapure, S. P.; Biehl, E. R.; *Syn. Commun.*, 1990, 20, 3235) dissolved in $CH_2Cl_2$ (100 mL) was placed into a 500 mL 3-necked round-bottom flask equipped with a stirring bar. The solution was cooled to 0° C. (ice bath) and NOCl (Fluka) was bubbled through until the reaction mixture turned a brick-red color. The reaction mixture was stirred at 0° C. for 30 min and then at room temperature for 18 hours. The precipitate was collected and washed with $CH_2Cl_2$ (25 mL) to afford the product as a white solid (2.88 g, 17.0 mmol).

$^1$H NMR (400 MHz, DMSO-$d_6$, δ): 7.70 (s, 1H), 3.32 (s, 1H), 1.32 (s, 9H); mp: 218-219° C.

Part B: 2-Amino-2-cyano-N-(1,1-dimethylethyl)acetamide 13

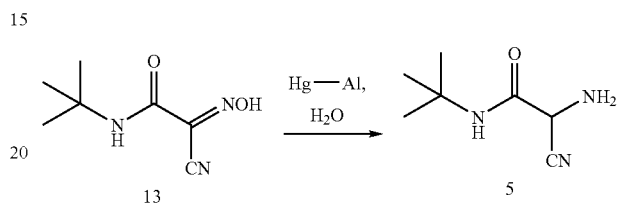

Oxime 13 (2.5 g, 14.78 mmol), Al amalgam (0.81 g) and distilled $H_2O$ (100 mL) were placed into a 250 mL round-bottom flask equipped with a stirring bar, nitrogen inlet, a gas outlet tube, and maintained under positive pressure of nitrogen. The reaction mixture was stirred at 2-10° C. (ice bath) for 2.5 hours, filtered, the filtrate extracted with $CH_2Cl_2$ (2×60 mL), and the combined organic layers were concentrated under reduced pressure to afford the product as an oil (1.62 g, 10.44 mmol). Concentration of the aqueous layer under reduced pressure afforded additional product 5 (0.41 g, 2.64 mmol).

$^1$H NMR (400 MHz, DMSO, δ): 7.68 (s, 1H), 4.34 (s, 1H), 2.78 (bs, 2H), 1.32 (s, 9H).

The Al amalgam used in this Step was prepared as follows: $HgCl_2$ (1.6 g, 5.89 mmol) was dissolved in 160 mL distilled $H_2O$ in a 250 mL round-bottom flask equipped with a stirring bar. The solution was cooled to 0-5° C. (ice bath), aluminum foil (4.0 g, 148.3 mmol), cut into small squares (≈0.5 to 1.0 cm$^2$), was added, and the mixture was stirred for 1.5 min. It was then filtered, and the solids were washed with MeOH (2×60 mL) and then t-BuOMe (60 mL), dried under vacuum (20 mm Hg, 3 hours) and stored under $N_2$.

Part C: Purification of Aminocyanoacetamide 14

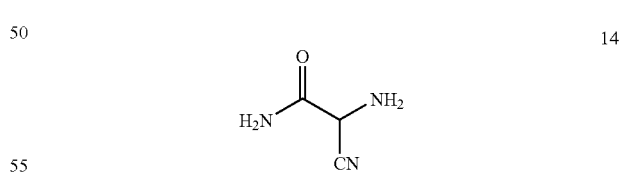

Aminocyanoacetamide 14 (60.0 g, 0.606 mol) (Aldrich, black solid) and acetone (2 L) were placed into a 5 L, three-necked flask equipped with a nitrogen inlet, a gas outlet tube, reflux condenser, thermometer, mechanical stirrer, and maintained under a positive pressure of nitrogen. The mixture was heated to reflux for 10 min with vigorous stirring, gradually cooled to room temperature, and then filtered. The organic solution was concentrated under reduced pressure to yield 55.2 g (0.557 mol) of 14. The product was dried in a vacuum oven (20 mm Hg, 20° C., 18 hours) and is a tan solid.

Part D: Preparation of 5-Amino-$N^1$-methyl-1H-imidazole-1,4-dicarboxamide 15

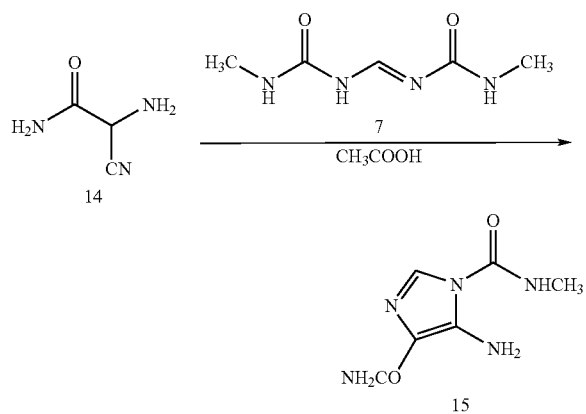

Aminocyanoacetamide 14 (80 g, 0.807 mol), urea 7 (139 g, 0.879 mol), and glacial acetic acid (0.96 L, 16.77 mol) (Fisher Scientific) were placed into a 2 L, three-necked flask equipped with a nitrogen inlet, a gas outlet tube, reflux condenser, thermometer, mechanical stirrer, and maintained under a positive pressure of nitrogen. The mixture was stirred vigorously at room temperature for 2 hours and then concentrated under reduced pressure. After removal of most of the acetic acid, 200 mL of t-BuOMe was added and the mixture was concentrated under reduced pressure. The residue (a viscous oil) was treated with MeOH/t-BuOMe (1:20, 2.5 L), and precipitation was induced by scratching the glass surface. The mixture was stirred for 30 min and the precipitate was collected by vacuum filtration. The solid was dried in an oven (20 mm Hg, 20° C., 18 hours) to yield 135 g of a grayish solid. The crude product was purified by slurrying in $H_2O$ (0.7 L) at room temperature for 1 hour. The solid product 15 was collected by filtration and was oven dried (20 mm Hg, 20° C., 18 hours) to yield 129 g of a grayish solid (0.680 mol, 97% pure against a standard sample by HPLC analysis). A standard sample of 5-amino-$N^1$-methyl-1H-imidazole-1,4-dicarboxamide 15 was prepared by recrystallization from $CH_3CN/H_2O$ (1:6); mp: 165-169° C.

$^1$H NMR (400 MHz, DMSO-$d_6$, δ): 8.50 (q, 1H), 7.67 (s, 1H), 6.9 (bd, 2H), 2.83 (d, 3H).

Part E: Preparation of 5-Amino-1H-imidazole-4-carboxamide hydrochloride 16.HCl from 5-Amino-$N^1$-methyl-1H-imidazole-1,4-dicarboxamide 15

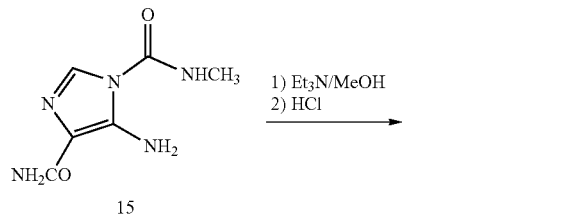

5-Amino-$N^1$-methyl-1H-imidazole-1,4-dicarboxamide 15 (10.72 g, 0.057 mol, 97% pure against a standard sample by HPLC analysis), $Et_3N$ (5 mL) and MeOH (100 mL) were placed into a 250 mL round-bottom flask equipped with a magnetic stir bar. The heterogeneous reaction mixture was heated at 80° C. (oil bath) for 4 hour with vigorous stirring, gradually cooled to room temperature (the reaction mixture is a dark homogeneous solution), and concentrated under reduced pressure. The residue (a viscous oil) was treated with t-BuOMe/acetone/MeOH (50 mL/20 mL/5 mL) and stirred for 2 hour. Precipitation was induced by scratching the glass surface. The precipitate was collected by vacuum filtration to yield 7.21 g of 5-amino-1H-imidazole-4-carboxamide (as free base). The free base was converted into 5-amino-1H-imidazole-4-carboxamide hydrochloride 16.HCl by slurrying in HCl/MeOH (2.6 M, 40 mL, 0.104 mol, prepared by bubbling HCl gas into MeOH). The solid product 16.HCl was collected by filtration and air dried (2 hour) to yield 8.5 g of product (0.051 mmol, 97% pure against an Aldrich sample by HPLC analysis). $^1$H NMR (400 MHz, $D_2O$, δ): 8.21 (s, 1H).

Part F: Preparation of 5-Amino-N-(1,1-dimethylethyl)-1H-imidazole-4-carboxamide 17

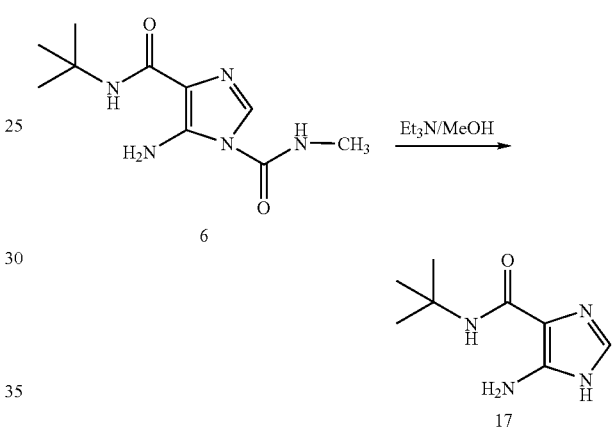

5-Amino-$N^4$-(1,1-dimethylethyl)-$N^1$-methyl-1H-imidazole-1,4-dicarboxamide 6 (10.4 g, 0.041 mol, 93% pure), MeOH (100 mL) and $Et_3N$ (5 mL) were placed into a 250 mL, three-necked flask equipped with a nitrogen inlet, a gas outlet tube, reflux condenser, thermometer, magnetic stirrer bar, and maintained under a positive pressure of nitrogen. The mixture was heated at 80° C. (oil bath) for 3 hour with vigorous stirring (when HPLC analysis indicated that no more starting material was present), gradually cooled to room temperature, and concentrated under reduced pressure. The gummy residue was treated with a solution of t-BuOMe (10 mL), n-heptane (100 mL) and acetone (2 mL), and stirred at room temperature for 1 hour. The resulting precipitate was collected by vacuum filtration and dried (20 mm Hg, 20° C., 18 hours) to yield 8.9 g (theoretical yield is 7.37 g) of 5-amino-N-(1,1-dimethyl-ethyl)-1H-imidazole-4-carboxamide 17 as a tan solid.

$^1$H NMR (400 MHz, $CDCl_3$, δ) 7.10 (s, 1H), 6.80 (s, 1H), 2.92 (d, 3H), 1.42 (s, 9H); mp: 186° C. (dec.)

Part G: Preparation of 5-Amino-1H-imidazole-4-carboxamide hydrochloride 16

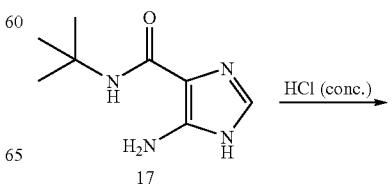

-continued

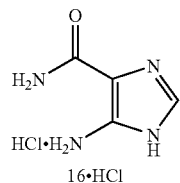

16·HCl

5-Amino-N-(1,1-dimethylethyl)-1H-imidazole-4-carboxamide 17 (8.9 g, theoretical amount is 7.37 g, 0.041 mol) and conc. HCl (20 mL) were placed into a 100 mL, three-necked flask equipped with a nitrogen inlet, a gas outlet tube, reflux condenser, thermometer, magnetic stirrer bar, and maintained under a positive pressure of nitrogen. The mixture was heated at 80° C. (oil bath) for 1 hour with vigorous stirring, gradually cooled to 0° C., yielding a precipitate, and then slowly added to 2-PrOH (30 mL). The solids were collected by vacuum filtration and washed with 2-PrOH (15 mL) to yield 4.97 g of product (0.030 mol, 97.5% pure against an Aldrich sample by HPLC analysis). The filtrate was concentrated under reduced pressure to give a gummy residue. The gummy residue was treated with MeOH (20 mL) and stirred for 20 min. The solids were collected by vacuum filtration and washed with MeOH (10 mL) to yield an additional 0.65 g of product (0.004 mol, 95% pure against an Aldrich sample by HPLC analysis). The combined amount of 5-amino-1H-imidazole-4-carboxamide hydrochloride 16.HCl was 5.62 g (0.034 mol, 97% pure against an Aldrich sample by HPLC analysis).

$^1$H NMR (400 MHz, D$_2$O, δ): 8.21 (s, 1H).

Analogs of Temozolomide, for example the 3-ethyl, 3-(1-propyl), 3-(1-butyl), and 3-(1-hexyl) analogs, can be prepared by similar methods.

All publications and patents cited herein are incorporated by reference to the same extent as if each individual publication or patent was specifically and individually indicated to be incorporated by reference.

Whereas a number of embodiments of this invention are described herein, it is apparent that these embodiments can be altered to provide other embodiments that utilize the compositions and processes of this invention. Therefore, it will be understood that the scope of this invention includes alternative embodiments and variations which are defined in the foregoing specification and by the claims appended hereto; and the invention is not to be limited to the specific embodiments presented herein by way of example.

The invention claimed is:

1. A compound of Formula II:

Formula II

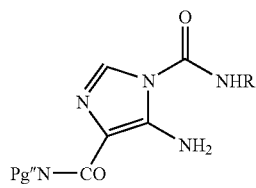

wherein Pg" is a divalent protecting group that is readily removable by hydrolysis or hydrogenolysis; or two monovalent protecting groups designated (Pg) that are readily removable by hydrolysis or hydrogenolysis; or a bulky monovalent protecting group (Pg) that is readily removable by hydrolysis or hydrogenolysis, together with a hydrogen atom and R is an alkyl group having from 1 to 6 carbon atoms and salts thereof, wherein the phrase "readily removable by hydrolysis or hydrogenolysis" refers to a divalent protecting group or two monovalent protecting groups or a bulky protecting group which can be removed by hydrogenolysis or hydrolysis when the compound of Formula II has been incorporated into a compound of Formula III Formula III

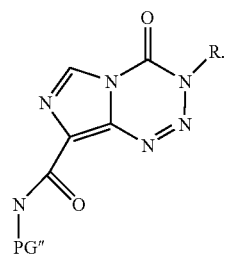

2. A compound as claimed in claim 1 wherein Pg" is Pg together with a hydrogen atom, wherein Pg is a 1,1-dimethylethyl group, and R is an alkyl group having from 1 to 4 carbon atoms.

3. A compound as claimed in claim 1 having the formula:

6

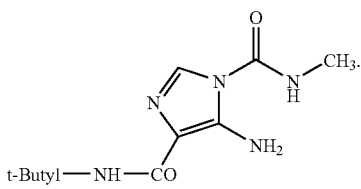

4. An acid addition salt of compound 6

6

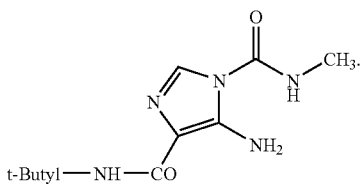

* * * * *